United States Patent
Otto et al.

(10) Patent No.: US 12,031,171 B2
(45) Date of Patent: Jul. 9, 2024

(54) FATTY ACID ESTERS AGAINST INFECTIONS IN FERMENTATIONS

(71) Applicant: PURAC BIOCHEM BV, Gorinchem (NL)

(72) Inventors: Roel Otto, Gorinchem (NL); Aldana Mariel Ramirez, Amsterdam (NL); Jenny Eelderink, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 79 days.

(21) Appl. No.: 16/329,910

(22) PCT Filed: Sep. 5, 2017

(86) PCT No.: PCT/EP2017/072249
§ 371 (c)(1),
(2) Date: Mar. 1, 2019

(87) PCT Pub. No.: WO2018/046500
PCT Pub. Date: Mar. 15, 2018

(65) Prior Publication Data
US 2019/0241916 A1 Aug. 8, 2019

(30) Foreign Application Priority Data
Sep. 6, 2016 (EP) .................................. 16187414

(51) Int. Cl.
| | |
|---|---|
| *C12P 7/44* | (2006.01) |
| *C12N 1/16* | (2006.01) |
| *C12N 1/20* | (2006.01) |
| *C12P 7/06* | (2006.01) |
| *C12P 7/16* | (2006.01) |
| *C12P 7/18* | (2006.01) |
| *C12P 7/52* | (2006.01) |
| *C12P 7/56* | (2006.01) |

(52) U.S. Cl.
CPC ................ *C12P 7/44* (2013.01); *C12N 1/16* (2013.01); *C12N 1/20* (2013.01); *C12P 7/06* (2013.01); *C12P 7/16* (2013.01); *C12P 7/18* (2013.01); *C12P 7/52* (2013.01); *C12P 7/56* (2013.01)

(58) Field of Classification Search
CPC ...... C12P 7/44; C12P 7/06; C12P 7/18; C12P 7/52; C12P 7/56; C12P 17/04; C12P 7/46; C12N 1/16; C12N 1/14; C12N 1/20
See application file for complete search history.

(56) References Cited

U.S. PATENT DOCUMENTS

| | | | | |
|---|---|---|---|---|
| 3,275,503 A | * | 9/1966 | Marnett | B65D 81/28 514/547 |
| 3,883,669 A | | 5/1975 | Tsen et al. | |
| 3,958,033 A | * | 5/1976 | Sims | A23D 7/003 426/654 |
| 4,164,593 A | * | 8/1979 | Marnett | A21D 2/14 426/24 |
| 2006/0062832 A1 | | 3/2006 | Lopes | |
| 2007/0010856 A1 | | 1/2007 | Cohen | |
| 2008/0063755 A1 | * | 3/2008 | Gan | A21D 13/32 426/95 |
| 2009/0074926 A1 | * | 3/2009 | Otto | A23L 2/44 426/330.3 |
| 2009/0246318 A1 | | 10/2009 | Johansen | |
| 2010/0311832 A1 | | 12/2010 | Cazemier | |
| 2014/0273166 A1 | * | 9/2014 | Narendranath | C12P 7/08 435/254.21 |
| 2015/0057345 A1 | * | 2/2015 | Boomsma | A23K 20/105 514/494 |

FOREIGN PATENT DOCUMENTS

| | | |
|---|---|---|
| CA | 2660863 A1 | 2/2008 |
| CN | 101048064 A | 10/2007 |
| CN | 101801182 A | 8/2010 |

(Continued)

OTHER PUBLICATIONS

Machine translation of DE 4131714 A1 (published 1993) downloaded from the EPO on Oct. 20, 2020 (Year: 1993).*
Mendz et al. Arch. Microbiol. (1994) 162: 187-192 (Year: 1994).*
Dictionarysensagent webpage T http://dictionary.sensagent.com/Brettanomyces/en-en/#:~:text=Brettanomyces%20is%20a%20non-spore%20forming%20genus%20of%20yeast,teleomorph%20or%20spore%20forming%20form%20of%20the%20yeast.downloaded Mar. 24, 2022 (Year: 2022).*
Aug. 13, 2020 Australian Office Action issued in Australian Patent Application No. 2017324801.
Jun. 3, 2020 Translation of Japanese Office Action in Japanese Patent Application No. 2019-511364.
Jon J. Kabara et al.; "Fatty Acids and Derivatives as Antimicrobial Agents;" American Society for Microbiology; Jul. 1972; vol. 2 No. 1; pp. 23-28.

(Continued)

Primary Examiner — Allison M Fox
Assistant Examiner — Qing Xu
(74) Attorney, Agent, or Firm — Oliff PLC

(57) ABSTRACT

An antibacterial agent suppresses the growth of gram-positive contaminating bacteria. The antibacterial agent is selected from: a lactylate in accordance with the general formula $(R—O—CH(CH_3)—CO)_aO)_bM$; a glycerol ester in accordance with the general formula $CH_2OR_1—CHOR_2—CH_2OR_3$; and, mixtures thereof. In the general formulae: R represents a C4-C18 acyl group, $R_1$, $R_2$ and $R_3$ are each independently selected from H or a C4-C18 acyl group, the acyl group having an alkyl or alkenyl chain which may be branched or unbranched, with the proviso that at least one of $R_1$, $R_2$ or $R_3$ is H and at least one of $R_1$, $R_2$, or $R_3$ is an acyl group; M represents a proton ($H^+$) or a counter-cation chosen from the group Li, Na, K, Ca, Mg, Zn, Fe(II), Cu, Mn, Ag, ammonium or substituted ammonium having one or more (C1-4)alkyl optionally substituted with one or more hydroxyl.

8 Claims, No Drawings

(56) References Cited

FOREIGN PATENT DOCUMENTS

| CN | 102586368 A | 7/2012 | |
|---|---|---|---|
| CN | 103655536 A | 3/2014 | |
| DE | 4131714 A1 * | 5/1993 | ............... C02F 3/34 |
| JP | 2011-510045 A | 3/2011 | |
| WO | 01/06877 A1 | 2/2001 | |
| WO | 2004/037177 A2 | 5/2004 | |
| WO | 2004/107877 A1 | 12/2004 | |
| WO | WO-2008058727 A1 * | 5/2008 | ............ C12Q 1/045 |
| WO | WO-2009037269 A1 * | 3/2009 | ............ A01N 37/36 |
| WO | 2013/169231 A1 | 11/2013 | |
| WO | 2018/222184 A1 | 12/2018 | |

OTHER PUBLICATIONS

Schumacher et al., "Isolation and Structure Determination of an Antimicrobial Ester from a Marine Sediment-Derived Bacterium" American Chemical Society and American Society of Pharmacognosy. 2003. pp. 1291-1294.

Limayem et al., "Alternative Antimicrobial Compounds to Control Potential Lactobacillus Contamination in Bioethanol Fermentations" Jounral of Environmental Science and Health, 2011. pp. 709-714.

Rückle et al., "Hop Acids can Efficiently Replace Antibiotics in Ethanol Production" International Sugar Journal, vol. 108, No. 1287, 2006, pp. 139-147.

Nov. 7, 2017 Written Opinion of the International Searching Authority issued in International Patent Application No. PCT/EP2017/072249.

Nov. 7, 2017 International Search Report issued in International Patent Application No. PCT/EP2017/072249.

Chang et al. "Homofermentative production of D(−) or L(+) lactate in metabolically engineered *Escherichia coli* RR1". Applied and Environmental Microbiology, vol. 65, No. 4, Apr. 1999, pp. 1384-1389.

Milne et al., Sourcebook of Methods of Analysis for Biomass and Biomass-Conversion Processes. SERI/SP-220-3548. Golden, CO: Solar Energy Research Institute, Feb. 1990, pp. 1-428.

Jun. 29, 2020 European Office Action isussed in European Patent Application No. 17 772317.8.

Mar. 18, 2021 Translation of Japanese Office Action issued in Japanese Patent Application No. 2019-511364.

Dec. 23, 2021 Office Action issued in Chinese Patent Application No. 201780053659.5.

Nov. 19, 2021 Office Action issued in Malaysian Patent Application No. PI2019001196.

Jun. 5, 2023 Office Action issued in European Patent Application No. 17 772 317.8.

Nov. 20, 2023 Office Action issued in Chinese Patent Application No. 201780053659.5.

"Microbiology", China Agricultural University Press, Aug. 2015, p. 115.

* cited by examiner

FATTY ACID ESTERS AGAINST INFECTIONS IN FERMENTATIONS

TECHNICAL FIELD OF THE INVENTION

The present invention pertains to a method for suppressing the growth of gram-positive bacteria in culturing gram-negative bacteria, moulds and yeasts. In particular, the present invention relates to antibacterial agents which comprise a lactylate, a glycerol ester or a mixture thereof and to the use of such agents in fermenter cultures.

BACKGROUND OF THE INVENTION

Danger of infection with other microorganisms is one of the problems that is common to all microbiological processes in which pure cultures are used. This danger applies particularly to large industrial fermentation processes where the risk of contamination with other microorganisms is larger due to the scale of the process as compared to laboratory fermenter processes.

In yeast fermentation, workers have sought to mitigate the risk of bacterial contamination by using bacterial control agents. These agents include, for example, (natural) antibiotics and sulphite at a concentration which does not affect the viability of the yeast but which prevents outgrowth of contaminating bacteria. Details of such agents are disclosed in: Rückle et al., *Hop acids as natural anti-bacterials can efficiently replace antibiotics in ethanol production*, International Sugar Journal 108: 139-147 (2006); and, Limayem et al., *Alternative antimicrobial compounds to control potential Lactobacillus contamination in bioethanol fermentations*, Journal of Environmental Science and Health, Part B 46(8): 709-714, (2011).

Nowadays, genetically modified bacteria are often used as the production strain for a number of fermentation products. An example is the use of *Escherichia coli* capable of producing R-lactic acid, as described in Chang et al. *Homofermentative production of D(−)or L(+) lactate in metabolically engineered Escherichia coli RR1*, Applied and Environmental Microbiology 65(4): 1384-1389 (1999). Although this organism was demonstrated to grow on a relatively simple and cheap, chemically defined medium, it was repeatedly observed that cultures of this organism could easily become infected. The contaminants appeared to be spore forming micro-organisms, or gram-positive micro-organisms. Among the contaminating gram positive bacteria are also pathogenic bacteria such as: *Enterococcus, Clostridium, Listeria, Staphylococcus*, various *Bacillus* species, and *Streptococcus*. Contaminants are undesirable because they can seriously compromise the optical purity of the lactic acid and they can produce other fermentation products and thereby lower the fermentation yield. There are therefore good reasons to suppress the outgrowth of these micro-organisms.

It is an object of the present invention to stabilize the production process and in particular the yield of the fermentation product of interest.

It has now been found that the addition of lactylates and/or glycerol esters of medium chain fatty acids specifically inhibits the outgrowth of gram-positive bacteria when culturing gram-negative bacteria or moulds and yeasts. Upon adding an effective amount of a lactylate, a glycerol ester or a mixture thereof, the producer microorganisms continue to grow in a fermenter but the growth of contaminating gram-positive bacteria is prevented or suppressed. This ensures that the fermentation process is not disturbed by outgrowth of unwanted microorganisms, unwanted side-products and inefficient use of energy sources. It furthermore diminishes the required additive amount of bacterial contaminating control agents such as antibiotics.

A lactylate refers to a compound having an acyl group from the fatty acid attached to one (monolactylates) or several lactic acid molecules (dilactylates etc.) and a proton (H+) or another cation attached to the terminal carboxylate. The fatty acid moiety consists typically of a hydrocarbon chain attached to a carboxyl group at the end. The hydrocarbon chain can contain different numbers of carbon atoms, and the bonds between the carbon atoms can be saturated or unsaturated.

Lactylates are known surfactants. These surfactants are made by reacting R-lactic acid or S-lactic acid or any mixture of these two with a fatty acid and concurrently neutralizing with a base. Lactylates are well known in the food industry and are used in personal care applications to improve skin feel, skin softness and moisturization, and to reduce tackiness during wet to dry transition after product application. It is known that certain lactylates possess antimicrobial properties. US2007/010856 (Cohen et al.) describes sutures treated with inter alia a lactylate as an antimicrobial compound. US2006/062832 (Lopes) describes a wipe composition comprising a lactylate as an antimicrobial compound. WO2004/037177 (Eveready Battery Inc.) describes an antibacterial shaving foam or gel formulation which contains lactylate as an antimicrobial compound.

WO01/06877 (Rhodia) describes the use of lactylates in combination with hop acids in food; the hop acids have activity against gram positive bacteria and lactylates are proposed as one possible adjunct ingredient amongst a very broad range of food-grade emulsifiers (page 6). The specific use of lactylates is not exemplified and the fact that lactylates have an individual activity against gram positive bacteria is not recognised in this reference.

It is noted that WO 2004/107877 (Purac Biochem BV) describes an antimicrobial composition comprising a mixture of lactic acid or a derivative thereof and an inorganic acid. The composition is described as an antimicrobial in general. The use against *Salmonella* and *Escherichia coli* is specified. While lactylates are mentioned as possible lactic acid derivatives, their use is not further elucidated. There is nothing in this reference that teaches or suggests a particular efficacy of lactylates against gram-positive bacteria as compared to gram-negative bacteria.

STATEMENT OF THE INVENTION

In accordance with the first aspect of the present invention, there is provided a fermentation medium comprising:
  a substrate for microbial growth; and,
  as an exogenous, added ingredient, an antimicrobial agent selected from:
    i) a lactylate in accordance with Formula 1, (R—(O—CH(CH$_3$)—CO)$_a$O)$_b$M    (Formula 1);

ii) a glycerol ester in accordance with Formula 2,

CH$_2$OR$_1$—CHOR$_2$—CH$_2$OR$_3$    (Formula 2); and, iii) a mixture of such compounds,
  wherein:
    R represents a C4-C18 acyl group, the acyl group having an alkyl or alkenyl chain which may be branched or unbranched;
    R$_1$, R$_2$ and R$_3$ each independently represent H or a C4-C18 acyl group, the acyl group having an alkyl or alkenyl chain which may be branched or unbranched, with the proviso that at least one of $R_1$, $R_2$ or $R_3$ is H and at least one of $R_1$, $R_2$, or $R_3$ is an acyl group;

M represents a proton ($H^+$) or a counter-cation chosen from the group Li, Na, K, Ca, Mg, Zn, Fe(II), Cu, Mn, Ag, ammonium or substituted ammonium having one or more (C1-4)alkyl optionally substituted with one or more hydroxy;

a is an integer of from 1 to 3; and, b is 1 or 2 equaling the valency of M.

For completeness, the term "mixture of such compounds" as used herein denotes that the antibacterial agent may contain: two or more compounds which conform to Formula 1; two or more compounds which conform to Formula 2; or, mixtures of compounds as defined in Formula 1 and Formula 2.

The fermentation medium may comprise the antibacterial agent in an amount of from 0.001 to 0.5 wt. %, preferably from 0.025 to 0.5 wt. %, based on the total weight of the medium. In an alternative expression, the fermentation medium may comprise the antibacterial agent at a concentration of from 0.1 to 1000 mg/L, preferably from 0.5 to 500 mg/L and more preferably of from 1 to 100 mg/L of fermentation medium.

The fermentation medium may further comprise an inoculant comprising a culture of gram-negative bacteria, moulds or yeasts. In forming such a medium, the antibacterial agent may be added to the medium prior to, after or together with that culture of gram-negative bacteria, moulds or yeasts. These modes of addition are not mutually exclusive and the present invention does not preclude the addition of the antibacterial agent at more than one stage of the fermentation.

In a preferred embodiment, however, the fermentation medium is obtained by: contacting the substrate for microbial growth with said antibacterial agent for a period of from 1 minute to 48 hours, preferably of from 1 to 24 hours, before inoculation of the fermentation medium with the fermenting micro-organism.

In an alternative or additional embodiment, the fermentation medium may be obtained by adding said antibacterial agent to an aqueous, recycled process stream that is a stream which is derived from a product of the fermentation but which is recycled as an input to the fermentation medium for inter alia water balance.

In accordance with a second aspect of the present invention, there is provided an inoculant for a fermentation medium comprising:

a culture of gram-negative bacteria, moulds or yeasts; and, an antibacterial agent selected from:

i) a lactylate in accordance with Formula 1,

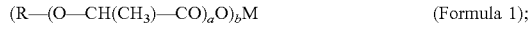
(R—(O—CH(CH$_3$)—CO)$_a$O)$_b$M    (Formula 1);

ii) a glycerol ester in accordance with Formula 2,

CH$_2$OR$_1$—CHOR$_2$—CH$_2$OR$_3$    (Formula 2); and, iii) a mixture of such compounds, wherein:

R represents a C4-C18 acyl group, the acyl group having an alkyl or alkenyl chain which may be branched or unbranched;

$R_1$, $R_2$ and $R_3$ each independently represent H or a C4-C18 acyl group, the acyl group having an alkyl or alkenyl chain which may be branched or unbranched, with the proviso that at least one of $R_1$, $R_2$ or $R_3$ is H and at least one of $R_1$, $R_2$, or $R_3$ is an acyl group;

M represents a proton (H+) or a counter-cation chosen from the group Li, Na, K, Ca, Mg, Zn, Fe(II), Cu, Mn, Ag, ammonium or substituted ammonium having one or more (C1-4)alkyl optionally substituted with one or more hydroxy;

a is an integer of from 1 to 3; and, b is 1 or 2 equaling the valency of M.

This second aspect of the invention prevents the contamination of the inoculant with gram-positive bacteria. Upon inoculating the fermentation medium, the anti-bacterial agent becomes dispersed in that medium where it can continue to suppress or prevent the growth of gram-positive bacteria which might be introduced as contaminants of the medium.

The present invention also provides for the use of an antibacterial agent for suppressing the growth of gram-positive contaminating bacteria in culturing gram-negative bacteria, moulds or yeasts, said antibacterial agent being selected from: a lactylate in accordance with Formula 1, as defined hereinabove; a glycerol ester in accordance with Formula 2, as defined hereinabove; or, a mixture of such compounds.

In accordance with a further aspect of the present invention, there is provided a method for preventing or reducing microbial infections caused by gram-positive bacteria in a fermenter culture of gram-negative bacteria, said method comprising adding to the culture an effective amount of an antimicrobial agent selected from: a lactylate in accordance with Formula 1, as defined hereinabove; a glycerol ester in accordance with Formula 2, as defined above; and, a mixture of such compounds.

And, in accordance with a final aspect of the invention, there is provided a method for obtaining a fermentation product, said method being defined in the appended claims and comprising the steps of: providing a fermentation medium; and, introducing into said medium an inoculant comprising a culture of gram-negative bacteria, moulds or yeasts.

Definitions

The term "comprising" as used herein will be understood to mean that the list following is non-exhaustive and may or may not include any other additional suitable items, for example one or more further feature (s), component (s), ingredient (s) and/or substituent (s) as appropriate.

An activity or agent which is "antibacterial" means herein an activity or agent which is capable of killing and/or inhibiting growth of bacteria.

The term "microbial growth" is used herein in accordance with its standard meaning: as such, "microbial growth" refers to an increase in the number and/or metabolic activity of microbial cells, including bacteria, molds, fungi, and algae.

The term "fermentation medium" as used herein means a three phase (solid-liquid-gas) system which is retained within the fermentation vessel. The liquid phase contains water, dissolved nutrients, dissolved substrates for microbial growth and dissolved metabolites; the source of the water is not limited and includes, in particular, process waters, such as backset and/or thin stillage, scrubber water, evaporator condensate or distillate, side stripper water from distillation, or other fermentation product plant process water. The solid phase comprises individual cells, pellets, insoluble substrates for microbial growth and precipitated metabolic products.

In the context of microbial growth, the term "substrate" refers to any substance or compound that is converted or meant to be converted into another compound by the action of an enzyme. The term "substrate" is intended to encompass not only compounds that provide a carbon source suitable for use as a starting material, such as any biomass derived carbohydrate, but also intermediate metabolites used in a metabolic pathway associated with a microorganism. The fermentation medium may typically comprise, as a substrate, one or more fermentable carbohydrates, such as sugars.

The fermentation medium, including fermentation substrate and other raw materials used in the fermentation process of the invention may be processed—by milling, liquefaction, saccharification or the like—prior to or simultaneously with the fermentation process. Accordingly, the fermentation medium can refer to the medium before the fermenting micro-organism is added, such as, the medium in or resulting from liquefaction and/or saccharification, as well as the medium which comprises the fermenting organism, such as, the medium used in simultaneous saccharification and fermentation (SSF) or one-step fermentation processes. For completeness, in that embodiment mentioned above where the antibacterial agent is added to the fermentation medium before the inoculating micro-organism, this includes the addition of said agent during liquefaction and/or saccharification.

The term "fermentation vessel" as used herein means the vessel in which the fermentation reaction is carried out. The term "fermenter" may be used interchangeably with fermentation vessel.

As used herein "inoculant" means the original source of a complex microbial community which is intended to be added to the fermentation vessel but which does not limit the final composition of the microbial community; the final composition is determined by the operating conditions and productivity of the fermentation vessel. The inoculant is typically formed by propagation of the desired microorganism(s) in a suitable propagation tank, which tank is much smaller than the fermentation vessel.

The inoculant typically includes a culture of one or more "production strains" of microorganisms which may have been adapted by natural selection or by biotechnological means to produce the fermentation product of interest. An exemplary, but non-limiting, inoculant contains a culture of the yeast *Saccharomyces cerevisiae* for the production of ethanol.

The term "culture" is used in a manner known in the art to denote the propagation of microbial organisms, in particular production strains, in a predetermined culture media conducive to their growth. As used herein the term "fermenter culture" refers to a propagation of one or more productions strains of microorganisms present within said fermentation medium or within an inoculant suitable for said fermentation medium.

There is no intention to limit the gram-negative bacteria which may be cultured and utilized in the present invention as the production strains. Exemplary, but non-limiting, gram-negative bacteria include: *Escherichia coli*; *Acinetobacter, Bordetella; Brucella; Campylobacter, Cyanobacteria; Enterobacter, Erwinia; Franciscella; Helicobacter; Klebsiella; Legionella; Moraxella; Neisseria; Pantooea; Pasteurellaceae*, especially bacteria of the *Actinobacillus* genus, *Hemophilus* genus and *Pasteurella* genus; *Pseudomonas; Proteus; Salmonella; Selenomonadales*, especially bacteria of the *Propionispira, Propionispora* and *Schwartzia* genera; *Serratia; Shigella; Treponema; Vibrio;* *Yersinia;* and, *Zynomonas*. In an interesting embodiment, the fermenter culture or fermentation medium comprises one or more gram negative bacterium selected from the group consisting of: *Escherichia coli; Pseudomonas* species; and, *Pasteurellaceae* species.

Exemplary moulds which might be mentioned are moulds of the genera: *Aspergillus*, in particular *Aspergillus oryzae, Aspergillus terreus* and *Aspergillus niger; Rhizopus*, for instance *Rhizopus oligosporus* and *Rhizopus oryzae; Fusarium*, such as *Fusarium oxysporum; Mucor*, such as *Mucor racemosus; Cladosporium*, such as *Cladosporium herbarum; Penicillum*, such as *Penicillum expansum*; and, *Trichoderma*, such as *Trichoderma harzanium*.

Non-limiting examples of yeast genera which may be employed in the present invention include: *Brettanomyces; Candida; Dekkera; Pichia*; and, *Saccharomyces*.

The carbohydrates that a specific microorganism can ferment are either commonly known to the person of ordinary skill in the art or are easily accessible in the published, background literature. For completeness, common carbohydrates fermentable by lactic acid producing microorganisms include but are not limited to: $C_5$ sugars such as arabinose, xylose and ribose; $C_6$ sugars such as glucose, fructose, galactose, rhamnose and mannose; and, $C_{12}$ sugars such as sucrose, maltose and isomaltose.

The fermentable carbohydrates are primarily derived from starch-based or sugar-based feedstocks. Examples of feedstocks include, but are not limited to: corn, wheat, triticale, barley, cassava, rye, graded starch stream rendered from the aforementioned feedstocks, sugar cane, sugar beet, molasses, rice straw, potato waste, wood waste, switch grass, pine and other wood derivatives, municipal waste, food waste and beverage (alcoholic and non-alcoholic) industry waste. An exemplary, but non-limiting, feedstock for the fermentation by *Saccharomyces cerevisiae* is molasses. Where desired, the content of fermentable carbohydrates in biomass may be determined by methods known in the art. A particularly instructive disclosure is Milne et al., *Sourcebook of Methods of Analysis for Biomass Conversion and Biomass Conversion Processes*. SERI/SP-220-3548. Golden, CO: Solar Energy Research Institute, February 1990.

As an exemplary, but non-limiting list of fermentation products which may be produced by gram negative bacteria, moulds and yeasts, such as the aforementioned microorganisms, there might be mentioned: ethanol; 1,3-propanediol; glycerol; butanol; 1,4-butanediol; arabitol; xylitol; sorbitol; mannitol; acetoin; acetic acid; propionic acid; 3-hydroxy propionic acid; lactic acid; succinic acid; furandicarboxylic acid; fumaric acid; malic acid; adipic acid; citric acid; aconitic acid; glutamic acid; itaconic acid; levulinic acid; glutaric acid; aspartic acid; malonic acid; glycine; serine; threonine; lysine; isoprene; and, polyhydroxybutyrate. In an embodiment, the fermentation medium which comprises the antibacterial agent as defined in the present invention may be for the production of: ethanol; 1,3-propanediol; glycerol; butanol; 1,4-butanediol; arabitol; xylitol; sorbitol; mannitol; acetic acid; propionic acid; 3-hydroxy propionic acid; lactic acid; succinic acid; 2,5-furandicarboxylic acid; fumaric acid; malic acid; adipic acid; citric acid; aconitic acid; glutamic acid; itaconic acid; levulinic acid; glutaric acid; aspartic acid; malonic acid; and, mixtures thereof.

Good results have been obtained where the antibacterial agent has been added to a fermentation medium for the production of: 1,4-butanediol; propionic acid; 3-hydroxy-propionic acid; lactic acid; succinic acid; 2,5-furandicarboxylic acid; fumaric acid; malic acid; or itaconic acid. And it is most preferred to use said antibacterial agent in a fermentation medium for the production of: propionic acid; lactic acid; succinic acid; 1,4-butanediol; or, 2,5-furandicarboxylic acid. For completeness, where lactic acid is obtained as the fermentation product, the present invention also encompasses: the dimerization of that lactic acid to obtain lactide; the synthesis of polylactic acid by polycondensation of that lactic acid; and, the synthesis of polylactic acid by polymerization of lactide obtained from that lactic acid.

It will be recognised that the desired fermentation product(s) mentioned herein and obtainable by fermentation of a fermentable substrate with a suitable microorganism, will be produced as a component of a composition which typically further comprises: traces of the fermentable substrate; other substances produced by the microorganism; and, traces of the microorganism itself such as cellular debris and/or cellular components. The term "fermentation product" is intended to encompass both the crude product and the product after it has subjected to clarification, purification and/or concentration. Exemplary, but non-limiting methods of purification include one or more of: filtration, including micro- and ultrafiltration; distillation; (re-)crystallization; extraction; chemical treatment, such as acidification; ion exchange; activated carbon treatment; and, electrodialysis.

As is known in the art, Gram-positive bacteria are stained dark blue or violet by gram staining, mainly due to a high amount of peptidoglycan in their cell wall. The present invention is concerned with suppressing or preventing the growth of such bacteria in fermenter cultures. The invention is particularly concerned with suppressing or preventing the growth of Gram positive bacteria comprising: Enterococci; *Clostridium*, in particular *Clostridium perfringens* and *Clostridium pasteurianum*; *Listeria*, in particular *Listeria monocytogenes* and *Listeria innocua*; *Staphylococcus*, in particular *Staphylococcus aureus*; various *Bacillus* species, in particular *Bacillus anthracis, Bacillus cereus* and *Bacillus subtilis*; and, *Streptococcus*.

As used herein, the term "acyl group" means a functional group derived from removing a hydroxyl group from a carboxylic acid and which has the formula $R_xCO$— wherein $R_x$ is an alkyl group or alkenyl group that is attached to the CO group with a single bond. One or more unsaturated bonds may be present in the alkenyl group. The total number of carbon atoms in the acyl chain thus is the number carbon atoms in the $R_x$ chain+1. The term (C4-C18)acyl means an acyl group having 4-18 carbon atoms.

As used herein a glycerol ester bearing only one C4-C18 acyl group side-chain is termed a (C4-C18)glycerol monoester, a glycerol ester that bears two C4-C18 acyl groups is termed a (C4-C15)glycerol di-ester. Mixtures of said esters may be termed (C4-C18)glycerol mono/di-esters or (C4-C18)glycerol mono/di.

Exemplary acyl groups include: C6 acyl groups such as iso-hexanoyl groups; C8 acyl groups such as iso-octanoyl groups; C10 acyl groups such as decanoyl groups; C12 acyl groups such as lauryl (dodecanoyl); C14 acyl groups such as myristyl (tetradecanoyl) groups; C16 acyl groups such as cetyl and palmityl (hexadecanoyl) groups; and, C18 acyl groups such as octadecanoyl.

DETAILED DESCRIPTION OF THE INVENTION

Broadly, the compounds defined in Formula 1 and Formula 2 above are used for suppression of the growth of gram-positive contaminating bacteria in culturing gram-negative bacteria, moulds or yeasts through the addition of one or more of these compounds to the culture media. In suppressing the growth of gram-positive contaminating bacterial, it is possible to improve production of the desired fermentation product.

The present invention does not preclude the addition, as the antibacterial agent, of two or more compounds which conform to Formula 1 or two or more compounds which conform to Formula 2. Moreover, mixtures of compounds as defined in Formula 1 and Formula 2 may also be used.

The total amount of antibacterial agent administered to the fermentation medium, inoculum or fermenter culture is such that it is effective to suppress, prevent or reduce contaminations caused by gram-positive bacteria. The exact amount of antibacterial agent will depend on a number of factors such as the particular agent used, the production strain being cultured, the type of medium and the energy source. In most embodiments however, the fermentation medium or other culture medium will contain from 0.001 to 0.5 wt. %, preferably from 0.025 to 0.5 wt. %, and more preferably from 0.1 to 0.5 wt. % based on the total weight of the medium, of the defined antibacterial agent.

In addition to the aforementioned antibacterial agent based on lactylates and/or glycerol ester, the fermentation medium may comprise at least one adjunct antimicrobial ingredient which has efficacy against gram positive bacteria but which does not substantially effect gram negative bacteria. Such adjunct ingredients may be added directly to the fermentation medium as an exogenous ingredient. Additionally or alternatively, the adjunct ingredients may be included in an inoculant for the fermentation medium.

In an embodiment, the fermentation medium, inoculant or fermenter culture may comprises up to 1 wt. %, based on the total weight of the medium, of an adjunct antimicrobial agent selected from the group consisting of: lysozyme; nisin; pediocin; ε-Polylysine; Protamin; Hop beta acids; rosin acids; pimelic acid; benzoic acid; p-hydroxybenzoic acid; salicylic acid; cinnamic acid; citric acid; saturated fatty acids with a chain length of from 8 to 16 carbon atoms; sugar esters of saturated fatty acids with a chain length of from 8 to 16 carbon atoms; and, mixtures thereof. In an alternative expression, the fermentation medium may comprise up to 2000 mg/L of said adjunct antimicrobial agent.

Formula 1

The lactylates employed in the present invention possess a structure according to Formula 1 herein-below:

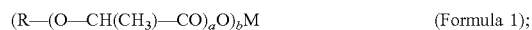

(R—(O—CH(CH$_3$)—CO)$_a$O)$_b$M  (Formula 1);

R represent a C4-C18 acyl group, preferably a C8 to C14 acyl group, more preferably a C10-C14 acyl group and most preferably a C12-C14 acyl group.

M represents a proton (H$^+$) or a counter-cation chosen from the group Li, Na, K, Ca, Mg, Zn, Fe(II), Cu, Mn, Ag, ammonium or substituted ammonium having one or more (C1-4)alkyl optionally substituted with one or more hydroxyl groups. Preferably M is selected from the group consisting of Na, K, Ca and Mg. More preferably, M is Na.

The group (O—CH(CH$_3$)—CO)O represents a lactyl radical of either the R or S configuration (as defined in Section E in the 1979 edition of the IUPAC *Nomenclature of Organic Chemistry*) derived from R- or S-lactic acid. The group might also represent a mixture of such stereo-isomeric configurations.

The value of b is equal to the valency of M. "b" thereby attains the value of 1 if M is a proton (H$^+$) or a monovalent cation such as Na, K, Ag, ammonium (NH$_4$) or substituted ammonium. "b" attains the value of 2 where M is a divalent cation such as Ca, Mg, Zn, Mn, Fe(II) or Cu.

The value of "a" may be from 1 to 3, with 1 being preferred. Lactylates in which "a" is 1 are termed monolactylates; compounds where "a" is 2 are termed dilactylates; and, compounds where "a" is 3 are termed trilactylates. Monolactylates (a=1) are preferred for use herein. However, it is noted that where a monolactylate is included in the antimicrobial agent, this does not preclude the presence of trace amounts of dilactylates and trilactylates therein; the higher order species can arise in the course of synthesizing the monolactylate.

Exemplary lactylates of Formula 1 which find utility as anti-bacterial agents in the present invention include but are not limited to: dodecanoyl-lactylate (C12-lactylate); tetradecanoyl-lactylate (C14-lactylate); hexadecanoyl-lactylate (C16-lactylate); octadecanoyl lactylate (C18:0-lactylate) and, octadec-9-enoyl-lactylate (C18:1-lactylate).

Methods of synthesis of such lactylates are known in the art. Mention may be made of: U.S. Pat. No. 3,883,669 (Tsen et al.); U.S. Pat. No. 4,146,548 (Forsythe); Elliger, *A convenient preparation of pure stearoyl-2-lactylic acid*, Journal of Agricultural and Food Chemistry 27: 527 (1979); and, WO 2012/036693 (Caravan Ingredients Inc.). Further, crude lactylates obtained in such synthetic methods may be purified by conventional methods, including but not limited to: filtration; centrifugation; distillation; crystallization; extraction; and, chromatography.

Formula 2

The glycerol esters suitable for use as antibacterial agents in the present invention are defined in Formula 2:

$CH_2OR_1$—$CHOR_2$—$CH_2OR_3$ (Formula 2)

$R_1$, $R_2$ and $R_3$ each independently represent H or a C4-C18 acyl group with the proviso that at least one of $R_1$, $R_2$ or $R_3$ is H and at least one of $R_1$, $R_2$, or $R_3$ is an acyl group.

In a first embodiment, one or two of $R_1$, $R_2$ or $R_3$ are C6-C14 acyl groups and the remaining $R_n$ groups are H. Preferably, one or two of $R_1$, $R_2$ and $R_3$ are C8 acyl groups and the remaining $R_n$ groups are H.

It is noted that the present invention does not preclude the use of a mixture of glycerol mono- and di-esters within the antibacterial agent. For example, good results have been obtained from the use of (C8)glycerol mono/di-esters.

Methods of synthesis of such mono- and di-esters are known in the art. For example, the commercial synthesis of C4-C18 esters of glycerol is typically carried out by two different routes: direct esterification of the fatty acid with the glycerol (glycerolysis), catalyzed by a homogeneous acid, such as sulphuric or sulfonic acids; or, by transesterification of triglycerides and polyalcohol catalyzed by alkaline hydroxides like NaOH, KOH or Ca(OH)$_2$ and sodium salts of low molecular weight alcohols, such as methanol. Reference may also be made to: Mostafa et al. *Production of mono-, di-, and triglycerides from waste fatty acids through esterification with glycerol* Advances in Bioscience and Biotechnology, 2013, 4, 900-907; Hyun et al. *A single step non-catalytic esterification of palm fatty acid distillate (PFAD) for biodiesel production*. Fuel, 93, 373-380 (2012). Further, crude glycerol esters obtained in such synthetic methods may be purified by conventional methods, including but not limited to: filtration; centrifugation; distillation; crystallization; extraction; and, chromatography.

The invention is further illustrated by the following examples, which show the inventive merits of this invention, without the invention being limited thereto or thereby.

EXAMPLES

AMCET 200C: C8-glycerol mono- and diester mixture, purchased from Corbion Caravan, Lenexa, Kansas, U.S.

AMCET 3400E: A mixture of decanoyl-lactylate (C10-lactylate) and dodecanoyl-lactylate (C12-lactylate, purchased from Corbion Caravan, Lenexa, Kansas, U.S.A.

AMCET 4530E: A mixture of dodecanoyl-lactylate (C12-lactylate) and tetradecanoyl-lactylate (C14-lactylate), purchased from Corbion Caravan, Lenexa, Kansas, U.S.A.

ATCC: American Type Culture Collection, Manassas, Virginia, U.S.A.

Bioscreen C: A culture system available from Oy Growth Curves Ab Ltd, Helsinki, Finland. The Bioscreen C kinetically measures the development of turbidity (growth) by vertical photometry in up to 200 wells simultaneously.

EMPLEX: C18-lactylate, purchased from Corbion Caravan, Lenexa, Kansas, U.S.

MIC: Minimal Inhibitory Concentration, as measured in an optical density test, is the lowest concentration at which the increase in absorbance of a culture did not exceed the threshold value, which was defined as the average increase in absorbance value of the blanks plus three times the standard deviation.

Olacta: Octadecenoyl-lactylate (C18:1-lactylate) purchased from Corbion Caravan, Lenexa, Kansas, U.S.A.

Pationic 122A: A mixture of two lactylates, specifically sodium decanoyl lactylate (sodium caproyl lactylate) and sodium dodecanoyl lactylate (sodium lauroyl lactylate) in a 1.3:1 mol ratio, purchased from Corbion Caravan, Lenexa, Kansas, U.S.A.

Example 1: Effect of Tetradecanoyl-Lactylate (C14-Lactylate) on Mixed Cultures of *Escherichia coli* and *Clostridium pasteurianum*

To determine whether tetradecanoyl-lactylate (C14-lactylate) could prevent *Clostridium pasteurianum* JEG2 (NCCB 100154, NCCB: Netherlands Culture Collection of Bacteria, Utrecht, Netherlands) from growing in a culture of a bio-engineered homolactic R-lactic acid producing *Escherichia coli* TG128 (NRRL B-30962, NRRL: Agricultural Research Service Culture Collection, National Center for Agricultural Utilization Research, Peoria, Illinois, U.S.A.) three different fermentations were set up and carried out simultaneously. These fermentations were:

i) Fermenter 1: *Escherichia coli* TG128 pure culture fermentation;
ii) Fermenter 2. *Escherichia coli* TG128 mixed with *Clostridium pasteurianum* JEG2;
iii) Fermenter 3. *Escherichia coli* TG128 mixed with *Clostridium pasteurianum* JEG2 with 0.05% (w/v) tetradecanoyl-lactylate (C14-lactylate: Corbion Caravan, Lenexa, Kansas, U.S.A.) addition.

All three fermentations were carried out in sterile 7 litre fermenters. Fermenter 1, 2 and 3 received 3.5 l sterile growth medium of the following composition: 3.25 l demineralised water, 385 g glucose monohydrate, 12.25 g di-ammonium phosphate, 17.75 g di-potassium hydrogen phosphate, 12.25 g potassium dihydrogen phosphate, 3.5 ml of a 1 M solution of betaine-hydrochloride, 5.25 ml of a 1 M solution of MgSO$_4$ (magnesium sulphate), 3.5 ml of a 1 M solution of CaCl$_2$) (calcium chloride) and 5.25 ml of a trace metal solution. The trace element solution contains per liter: 1.6 g FeCl$_3$(iron(111)-chloride), 0.2 g CoCl$_2$.6H$_2$O (cobalt-chloride), 0.1 g CuCl$_2$ (copper-chloride), 0.2 g ZnCl$_2$.4H$_2$O (zinc-chloride) 0.2 g NaMoO$_4$ (sodium-molybdate), H$_3$BO$_3$ (boric acid) and 10 ml 37% (w/w) HCl (hydrochloric acid). Fermentor 3 received 0.05% (w/v) tetradecanoyl-lactylate (C14-lactylate).

All three fermenters were equipped with a pH probe. The pH of the fermentation was controlled at a value of 6.5 by the addition of a slurry of $Ca(OH)_2$ in demineralised water. The concentration of the $Ca(OH)_2$ slurry was approximately 220 g/l. The temperature of the fermentors was kept constant at a value of 37° C.

Each fermenter (1, 2 and 3) was inoculated with 80 ml of an actively growing overnight culture of *Escherichia coli* TG128. Fermenters 2 and 3 were also inoculated with 1 ml of a culture of *Clostridium pasteurianum* JEG2 growing on brain heart infusion broth. Depending on the progress of the fermentations the fermenter cultures were operated for 25-35 hours after which they were analysed. The results of the (chemical) analyses are summarized in Table 1 herein below:

TABLE 1

| Component (g/l) | Fermenter 1 *Escherichia coli* TG128 | Fermenter 2 *Escherichia coli* TG128 + *Costridium pasteurianum* NCCB 100154 | Fermenter 3 *Escherichia coli* TG128 + *Clostridium pasteurianum* NCCB 100154 + Tetradecanoyl-lactylate |
| --- | --- | --- | --- |
| R-lactate | 82.6 | 28.2 | 81.8 |
| S-lactate | 0 | 2 | 0.3 |
| % enantiomeric excess: (R − S)/(R + S) | 100 | 86.8 | 99.3 |
| Ethanol | 0.07 | 0.4 | 0.08 |
| glucose | 1.9 | 14.4 | 2.3 |
| Formic acid | <0.2 | 2 | <0.2 |
| Acetic acid | 0.2 | 2.3 | 0.3 |
| Propionic acid | <0.1 | <0.1 | <0.1 |
| Butyric acid | <0.1 | 6.6 | 0.1 |
| Pyruvic acid | <0.1 | <0.1 | <0.1 |
| 2-hydroxy butyric acid | <0.1 | <0.1 | <0.1 |
| Glycolic acid | <0.5 | <0.5 | <0.5 |
| Oxalic acid | <0.2 | <0.2 | <0.2 |
| Sorbic acid | <0.1 | <0.1 | <0.1 |
| Fumaric acid | <0.2 | <0.2 | <0.2 |
| Succinic acid | 0.1 | <0.1 | <0.1 |
| Benzoic acid | <0.3 | <0.3 | <0.3 |
| Maleic acid | <0.2 | <0.2 | <0.2 |
| Malic acid | <0.5 | <0.5 | <0.5 |
| Citric acid | <0.5 | <0.5 | <0.5 |

12 Hours after inoculation it was observed that Fermenter 2 started to produce a large volume of foam and a putrid smell. Microscopic examination of the culture broth revealed the presence of large numbers of endospore bearing cells. This phenomenon is seen when *Clostridium pasteurianum* JEG2 is growing unrestricted.

Fermenter 3 which was also inoculated with a mixed culture of *Escherichia coli* TG128 and *Clostridium pasteurianum* JEG2 but which also received 0.05% (w/v) tetradecanoyl-lactylate ($C_{14}$-lactylate) produced no foam or putrid smell. Moreover, microscopic examination of the culture broth taken from Fermenter 3 showed that it contained no endospore bearing cells.

The performance of Fermenter 3 was in every respect similar to the performance of Fermenter 1 which was inoculated with a pure culture of *Escherichia coli* TG128. Moreover chemical analysis of fermentation broth (Table 1) showed that there is no difference in impurity profile between the *Escherichia coli* TG128 standard fermentation (Fermenter 1) and the *Escherichia coli/Clostridium pasteurianum* JEG2 mixed culture with tetradacanoyl-lactylate (Fermenter 3). The percent enantiomeric excess of the lactate produced in Fermenters 1 and 3 is close to 100 and only a small amount of S-lactate was detected in Fermenter 3, probably introduced by saponification of the lactylate ester.

The percent enantiomeric excess in Fermenter 2 on the other hand was considerably lower due to the unrestricted growth of *Clostridium pasteurianum* JEG2. Furthermore, the total amount of lactic acid produced in Fermenter 2 was also considerably lower. Percent enantiomeric excess is defined as: $((R-S)/(R+S))*100$ and where R and S represent the respective fractions of enantiomers in the R- and S-lactate containing fermentation broth.

Exactly the same results were obtained when Fermenter 3 was fortified with 0.025% (w/v) tetradecanoyl-lactylate (C14-lactylate) instead of 0.05% (w/v).

Example 2: Effect of Mixtures of Decanoyl-Lactylate (C10-Lactylate) and Dodecanoyl-Lactylate (C12-Lactylate) or Mixtures of Dodecanoyl-Lactylate (C12-Lactylate) and Tetradecanoyl-Lactylate (C14-Lactylate) on Mixed Cultures of *Escherichia coli* and *Clostridium pasteurianum*

In an identical experimental set up as described in Example 1, the efficacy of 0.05% (w/v) AMCET 3400E and 0.05% (w/v) AMCET 4530E to suppress the growth of *Clostridium pasteurianum* JEG2 in a culture of *Escherichia coli* TG128 was tested.

The performance of Fermenter 3 with either AMCET 3400E or AMCET 4530E was in every respect similar to the performance of Fermenter 1 which was inoculated with a pure culture of *Escherichia coli* TG128. Moreover, chemical analysis of fermentation broth showed that there is no difference in impurity profile between the *Escherichia coli* TG128 standard fermentation (Fermenter 1) and the *Escherichia coli/Clostridium pasteurianum* JEG2 mixed culture with AMCET 3400E or AMCET 4530E (Fermenter 3). The percent enantiomeric excess of the lactate produced in Fermenter 1 and 3 is close to 100 for AMCET 3400E and AMCET 4530E.

Example 3: In Vitro Tests of Lactylates Against *Clostridium perfringens*

The efficacy of lactylates as defined in Formula 1 and glycerol esters as defined in Formula 2 to inhibit growth was tested against *Clostridium perfringens* ATCC 13124 in a Bioscreen C culture system.

The optical density of the cultures was automatically measured at fixed time intervals at 420-580 nm using a wide band filter. The growth rate of the test organisms was determined at 30° C. In order to assure low oxygen conditions the Bioscreen was placed inside an anaerobic cabinet equipped with a type M-12 oxygen sensor (In Vivo$_2$ 400 hypoxia workstation, Biotrace International Plc, Bridgend, United Kingdom). The oxygen tension was regulated at 0% oxygen using a Ruskinn gas mixer module (Biotrace International Plc).

Brain heart infusion broth was prepared with varying amounts of different lactylates and glycerol esters as indicated in Table 2 herein below.

The following compounds were tested: Octanoyl-lactylate (C8-lactylate), Decanoyl-lactylate (C10-lactylate), Dodecanoyl-lactylate (C12-lactylate), Tetradecanoyl-lactylate (C14-lactylate), Hexadecanoyl-lactylate (C16-lactylate), Olacta (octadecenoyl-lactylate, C18:1-lactylate), AMCET 3400E, AMCET 4530E, C8-glycerol mono/di, C10-glycerol mono/di, C12-glycerol mono/di, C14-glycerol mono/di, Tetradecanoic acid (Myristic acid) and Sodium tetradecyl sulfate (Sodium myristyl sulfate).

TABLE 2

| Species | Concentration Range % (w/v) | Concentration Step size % (w/v) |
|---|---|---|
| Octanoyl-lactylate (C8-lactylate) | 0-0.5 | 0.1 |
| Decanoyl-lactylate (C10-lactylate) | 0-0.1 | 0.02 |
| Dodecanoyl-lactylate (C12-lactylate) | 0-0.01 | 0.002 |
| Tetradecanoyl-lactylate (C14-lactylate) | 0-0.01 | 0.001 |
| Hexadecanoyl-lactylate (C16-lactylate) | 0-0.01 | 0.002 |
| Olacta (Octadecenoyl-lactylate, C18:1- lactylate) | 0-0.1 | 0.02 |
| AMCET 3400E (C10/C12- lactylate) | 0-0.01 | 0.001 |
| AMCET 4530E (C12/C14- lactylate) | 0-0.01 | 0.001 |
| C8- glycerol mono/di | 0-0.5 | 0.05 |
| C10- glycerol mono/di | 0-0.1 | 0.01 |
| C12- glycerol mono/di | 0-0.01 | 0.001 |
| C14- glycerol mono/di | 0-0.01 | 0.001 |
| Tetradecanoic acid (Myristic acid) | 0-0.01 | 0.001 |
| Sodium tetradecyl sulfate (Sodium myristyl sulfate) | 0-0.01 | 0.001 |

Tetradecanoic acid (Myristic acid), Sodium tetradecyl sulfate (Sodium myristyl sulfate) were purchased from Sigma-Aldrich.

The pH of the media was adjusted to 6.0 with 9 M sulphuric acid using a Handylab pH 12 pH meter equipped with a Blueline 16 pH (micro) probe (No. 285129163). All media were sterilised by filtration using 0.45 µm cellulose acetate filters (Minisart syringefilter, sterile and non-pyrogenic, no. 16555, Sartorius, Göttingen, Germany) (9). 300 µl of each medium was transferred to a panel of a sterile Bioscreen Honeycombe 100 well plate (Thermo electron Oy, Vantaa, Finland). Completed well plates were stored at −30° C. until further use. Well plates were inoculated with 3 µl seed culture using a sterile Hamilton repeating dispenser (Hamilton, Bonaduz, Switzerland). Liquid seed cultures of *Clostridium perfringens* ATCC 13124 were prepared in screw-capped tubes (100×16 mm) containing 10 ml brain heart infusion broth (Oxoid CM225, Basingstoke, United Kingdom) for 24 hours at 30° C.

Table 3 shows the MIC values of the lactylates, glycerol esters, tetradecanoic acid (myristic acid) and sodium tetradecyl sulfate (sodium myristyl sulfate) for *Clostridium perfringens* ATCC 13124 in brain heart infusion broth. In the parentheses the number of repeats is given.

TABLE 3

MIC values of different fatty acid derivatives for *Clostridium perfringens* ATCC 13124 in brain heart infusion broth. (The number of repeats is provided in brackets.)

| Species | MIC value % (w/v) |
|---|---|
| Octanoyl-lactylate (C8-lactylate) | 0.05 (2) |
| Decanoyl-lactylate (C10-lactylate) | 0.04 (2) |
| Dodecanoyl-lactylate (C12-lactylate) | 0.002 (2) |
| Tetradecanoyl-lactylate (C14-lactylate) | 0.001 (2) |
| Hexadecanoyl-lactylate (C16-lactylate) | 0.002 (2) |
| Olacta (Octadecenoyl-lactylate, C18:1- lactylate) | 0.02 (2) |
| AMCET 3400E (C10/C12- lactylate) | 0.02 (3) |
| AMCET 4530E (C12/C14- lactylate) | 0.001 (3) |
| C8- glycerol mono/di | 0.1 (3) |
| | 0.2 (4) |
| C10- glycerol mono/di | 0.02 (2) |
| | 0.04 (2) |
| C12- glycerol mono/di | >0.01 (2) |
| C14- glycerol mono/di | >0.01 (4) |
| Tetradecanoic acid (Myristic acid) | >0.01 (3) |
| Sodium tetradecyl sulfate (Sodium myristyl sulfate) | 0.001 (3) |

It appears that even at very low concentration, lactylates and glycerol esters are capable of suppressing the growth of *Clostridium perfringens* ATCC 13124.

Example 4: Antimicrobial Properties of Some Lactylates and C8-Glycerol Mono/Di-Esters The efficacy of a selected number of different lactylates as defined in formula 1 and C8-glycerol mono/di ester (Caprylic mono/di) as defined in formula 2 to inhibit growth was tested against a selection of gram-positive and gram-negative bacteria in a Bioscreen C culture system. The optical density of the cultures was automatically measured at fixed time intervals at 420-580 nm using a wide band filter. The growth rate of the test organisms was determined at 30° C.

Brain heart infusion broth was prepared with varying amounts of lactylates or C8-glycerol mono/di ester (Caprylic mono/di). The following compounds were tested: AMCET 3400E; AMCET 4530E; EMPLEX; and, AMCET 200C.

The pH of the media was adjusted to 6.0 with 9 M sulphuric acid using a Handylab pH 12 pH meter equipped with a Blueline 16 pH (micro) probe (no. 285129163). All media were sterilised by filtration using 0.45 μm cellulose acetate filters (Minisart syringefilter, sterile and non-pyrogenic, no. 16555, Sartorius, Göttingen, Germany). 300 μl of each medium was transferred to a panel of a sterile Bioscreen Honeycombe 100 well plate (Thermo electron Oy, Vantaa, Finland). Completed well plates were stored at 4° C. until further use. Well plates were inoculated with 3 μl of the appropriate test culture using a sterile Hamilton repeating dispenser (Hamilton, Bonaduz, Switzerland.

Liquid seed cultures were prepared of the following cultures were used in this study:

*Escherichia coli* serotype 0157:$H_7$ (ATCC 700728);
*Escherichia coli* (ATCC 8739);
*Staphylococcus aureus* (ATCC 6538P);
*Listeria monocytogenes* (F2399);
*Listeria monocytogenes* (ATCC 7644);
*Listeria monocytogenes* NFPA 83 (Seman, D. L., A. C. Borger, et al. (2002) *Journal of Food Protection* 65(4): 651-658);
*Listeria monocytogenes* LCDC 861 (Seman, D. L., A. C. Borger, et al. (2002) Journal of Food Protection 65(4): 651-658);
*Listeria innocua* (ATCC 33090);
*Listeria innocua* TNO strain (TNO, Zeist, The Netherlands);
*Salmonella enterica* (ATCC 13076, S. *Enteritidis*);
*Salmonella enterica* (ATCC 13311, S. *Typhimurium*);

*Salmonella enterica* JAVA (NCTC 8458, NCTC: National Collection of Type Cultures, Porton Down, Salisbury, United Kingdom);
*Lactobacillus sakei* (DSMZ 20017, DSMZ: Deutsche Sammlung von Mikroorganismen and Zellkulturen GmbH, Braunschweig, Germany);
*Lactobacillus plantarum* (DSMZ 20174);
*Lactobacillus curvatus* (DSMZ 20019);
*Bacillus cereus* (ATCC 11778);
*Pseudomonas lundensis* (LMG 13517, LMG: Belgian Coordinated Collections of Microorganisms/LMG Bacteria Collection, Gent, Belgium); and,
*Pseudomonas fragi* (LMG 2191).

All cultures were transferred daily in screw capped tubes (100×16 mm) containing 10 ml brain heart infusion broth (Oxoid CM0225, Basingstoke, UK). *Lactobacillus* species were transferred in MRS broth (Oxoid CM0359). All cultures were incubated at 30° C. and without agitation.

We have studied the effects of different concentrations of AMCET 3400E, AMCET 4530E, EMPLEX and AMCET 200C.

The data, which is summarised in Tables 4 and 5 herein below, shows that Gram-positive bacteria are more susceptible to these compounds than Gram-negatives species. The data in Table 5 also shows that AMCET 200C is active against a much wider range of organisms than the lactylates and it encompasses also the Gram negative bacteria. The effective concentration of AMCET 200C (C8-glycerol mono/di) against gram-negative bacteria is 0.5-1% (w/w).

TABLE 4

Effect of AMCET 3400E, AMCET 4530E, EMPLEX and AMCET 200C on different Gram positive and Gram negative bacteria.

| Strain | AMCET 3400E (C10/C12-lactylate) | AMCET 4530E (C12/C14-lactylate) | Emplex | AMCET 200C (C8-glycerol mono/di) |
|---|---|---|---|---|
| *Listeria monocytogenes* LCDC 861 | + (+) | + (+) | − (−) | − (−) |
| *Listeria monocytogenes* NFPA 83 | + (+) | + (+) | − (−) | − (−) |
| *Listeria monocytogenes* ATCC 7644 | + (+) | + (+) | − (−) | − (−) |
| *Bacillus cereus* ATCC 11778 | + (+) | + (+) | − (−) | − (−) |
| *Staphylococcus aureus* ATCC 6538P | + (+) | + (+) | − (−) | − (−) |
| *Lactobacillus plantarum* DSM 20174 | + (−) | + (−) | − (−) | − (−) |
| *Lactobacillus curvatus* DSM 20019 | + (−) | + (−) | − (−) | − (−) |
| *Lactobacillus sakei* DSM 20017 | + (+) | + (+) | − (−) | − (−) |
| *Escherichia coli* ATCC 8739 | − (−) | − (−) | − (−) | − (−) |
| *Escherichia coli* O157:H7 ATCC 700728 | − (−) | − (−) | − (−) | − (−) |
| *Salmonella enterica* ATCC 13311 | − (−) | − (−) | − (−) | − (−) |
| *Salmonella enterica* ATCC 13076 | − (−) | − (−) | − (−) | − (−) |
| *Salmonella enterica* JAVA strain | − (−) | − (−) | − (−) | − (−) |
| *Pseudomonas lundensis* LMG 13517 | − (−) | − (−) | − (−) | − (−) |
| *Pseudomonas fragi* LMG 2191 | − (−) | − (−) | − (−) | − (−) |

Two concentration ranges were tested: 0-0.1% (w/w) and 0-0.01% (w/w). Within Table 4, the results for the 0-0.01% concentration range are shown in the brackets. A "+" sign indicates inhibition. Gram positive organisms are *Listeria, Bacillus, Staphylococcus* and *Lactobacillus*.

TABLE 5

Effect of AMCET 3400E, AMCET 4530E, EMPLEX and AMCET 200C on different Gram positive and Gram negative bacteria.

| Strain | AMCET 3400E (C10/C12-lactylate) | AMCET 4530E (C12/C14-lactylate) | Emplex | AMCET 200C (C8-glycerol mono/di) |
|---|---|---|---|---|
| *Listeria monocytogenes* F2399 | + | + | + | + |
| *Listeria monocytogenes* LCDC 861 | + | + | + | + |
| *Listeria monocytogenes* NFPA 83 | + | + | + | + |
| *Listeria monocytogenes* ATCC 7644 | + | + | + | + |
| *Listeria innocua* ATCC 33090 | + | + | + | + |
| *Listeria innocua* TNO strain | + | + | + | + |
| *Bacillus cereus* ATCC 11778 | + | + | + | + |
| *Staphylococcus aureus* ATCC 6538P | + | + | + | + |
| *Lactobacillus curvatus* DSM 20019 | NT | NT | NT | + |
| *Lactobacillus sakei* DSM 20017 | NT | NT | NT | + |
| *Escherichia coli* ATCC 8739 | NT | NT | NT | + |
| *Escherichia coli* O157:H7 ATCC 700728 | − | − | − | + |
| *Salmonella enterica* ATCC 13311 | − | − | − | + |
| *Salmonella enterica* ATCC 13076 | − | − | − | + |
| *Salmonella enterica* JAVA strain | − | − | − | + |
| *Pseudomonas lundensis* LMG 13517 | NT | NT | NT | − |
| *Pseudomonas fragi* LMG 2191 | NT | NT | NT | − |

The concentration range tested was: 0-1% (w/w). Within Table 5, a "+" sign indicates inhibition, NT: not tested. Gram positive organisms are *Listeria, Bacillus, Staphylococcus* and *Lactobacillus*.

Example 5: Ethanol Fermentation with *Saccharomyces cerevisiae*

This Example documents the effect of a low concentration of a lactylate blend within an ethanol fermentation with *Saccharomyces cerevisiae*, said fermentation running on cane-sugar molasses and being deliberately contaminated with a mixed culture of *Lactobacillus* species.

Cultures and Culture Conditions

*Saccharomyces cerevisiae* MUCL30115 was obtained from the Mycotheque de l'Université Catholique de Louvain (BCCM/MUCL, Louvain-la-Neuve, Belgium) and pre-cultured in a yeast-peptone-glucose broth (YPG). The YPG-broth contained, per litre of demineralized water: 40 g glucose monohydrate; 10 g Bacto™ Peptone (Becton, Dickinson and Company, Sparks, Maryland, USA); and, 5 g Bacto™ Yeast extract (Becton, Dickinson and Company, Sparks, Maryland, USA). The pH of the medium was adjusted to 6.0-7.0 with 1N HCl. Cultures were incubated in shake flasks at room temperature.

*Lactobacillus brevis* LMG11438 was obtained from the Laboratorium voor Microbiologie, Universiteit Gent (BCCM/LMG, Gent, Belgium). *Lactobacillus fermentum* AR748 and *Lactobacillus fructivorans* AR742 were obtained from Corbion Purac B.V., Gorinchem, The Netherlands. All strains were pre-cultured on MRS-broth (de Man et al (1960) *A medium for the cultivation of lactobacilli*. J. Appl. Bacteriology 23(1): 130-135) and incubated at 30° C. in stationary screw capped flasks. A mixed culture was prepared by mixing equal volumes of the three *Lactobacillus* cultures.

All fermentation experiments were carried out in 3 litre jacketed glass fermenters containing 0.5 litres of a liquid medium having the following composition: 50 g cane-sugar molasses (85° Brix); and, 450 ml demineralized water. The temperature of each fermentation was controlled at 30° C. using a circulating water-bath and the pH was controlled at 5.5 with 1N NaOH.

Two primary fermenters (A, B) were each inoculated with 50 ml of the actively fermenting *Saccharomyces* culture: both these cultures also received 10 ml of the mixed *Lactobacillus* culture. To one of these fermenters (A) was added a 0.5 ml of a solution containing 10% (w/w) Pationic 122A in order to study the effect of lactylates thereon.

After 24 hours of fermentation, 9-10 vol. % of inoculum was removed from each fermenter (A, B) and respectively transferred to further fermenters (A', B') containing fresh medium: the fermentation in the primary fermenters (A, B) was allowed to proceed. Using this back slopping technique, six to eight further transfers of inoculum were performed, each after 24 hours of fermentation in the source fermenter.

Analytical Methods

The amounts of L(+) lactic acid, D(-) lactic acid and residual glucose were determined using enzymic procedures. Specifically and each in accordance with the given manufacturer's protocol: glucose was assayed using the K-Gluc kit available from Megazyme International; D-lactic acid was assayed using the K-Date kit available from Megazyme International; and, L-Lactic acid was assayed using the L-Date kit available from Megazyme International.

Organic acids and ethanol were determined by Gas Chromatographic analysis.

Results

Table 6 below indicates the determined amounts of L(+) lactic acid, D(-) lactic acid and ethanol in the fermentations which have been contaminated with the mixed culture of *Lactobacillus* species. In those fermenting cultures of *Saccharomyces cerevisiae* which also contain Pationic 122A there is shown to be a significant lowering of the standing concentrations of L(+) and, in particular, D(-) lactic acid as compared to cultures which do not contain the lactylate blend. Moreover, the ethanol concentration of cultures of *Saccharomyces cerevisiae* which contain Pationic 122A is significantly elevated over those cultures in which the lactylate blend in absent. The positive effects of Pationic 122A could be maintained for at least 6-8 consecutive transfers.

TABLE 6

| Transfer No. | Pationic 122A Present | L(+) Lactic acid (g/l) | D(-) Lactic acid (g/l) | Ethanol (% w/w) |
|---|---|---|---|---|
| Molasses Fermentation with *Saccharomyces cerevisiae* contaminated with LAB mixed culture | | | | |
| 2 | No | 1.40 | 6.80 | 1.20 |
| 3 | No | 1.18 | 6.50 | 1.30 |
| 4 | No | 1.28 | 6.79 | 1.60 |
| 5 | No | 1.16 | 3.15 | 1.30 |

TABLE 6-continued

| Transfer No. | Pationic 122A Present | L(+) Lactic acid (g/l) | D(-) Lactic acid (g/l) | Ethanol (% w/w) |
|---|---|---|---|---|
| 6 | No | 1.42 | 3.31 | 1.60 |
| Average | | 1.29 | 5.31 | 1.40 |
| Molasses Fermentation with *Saccharomyces cerevisiae* contaminated with LAB mixed culture and in presence of Pationic 122A | | | | |
| 2 | Yes | 0.15 | 2.10 | 1.30 |
| 3 | Yes | 0.16 | 0.90 | 2.10 |
| 4 | Yes | 0.15 | 0.98 | 2.20 |
| 5 | Yes | 0.21 | 0.97 | 2.20 |
| 6 | Yes | 0.23 | 1.33 | 1.80 |
| Average | | 0.18 | 1.25 | 1.92 |

It will be apparent to those skilled in the art, upon consideration of the specification, that various modifications can be made in the disclosed embodiments without departing from the scope of the invention. It is therefore intended that the embodiments and examples be considered illustrative only, with the true scope of the invention being indicated by the following claims.

The invention claimed is:

1. A fermentation medium comprising:
   an inoculant comprising a culture of at least one production strain of *E. coli* or *Salmonella enterica*;
   a substrate for microbial growth, the substrate comprising one or more carbohydrates fermentable by the *E. coli* or *Salmonella enterica* of the inoculant; and
   as an exogenously added ingredient, an antimicrobial agent comprising a lactylate in accordance with Formula 1 or salt thereof in an amount from 0.025 to 0.5 weight %, based on the total weight of the fermentation medium, $$(R-(O-CH(CH_3)-CO)_aO)_bM \quad \text{(Formula 1)};$$

wherein in the Formula 1:
   the "R" represents a C4-C18 acyl group, the acyl group having an alkyl or alkenyl chain which may be branched or unbranched;
   the "M" represents a proton (H$^+$) or a counter-cation chosen from Li, Na, K, Ca, Mg, Zn, Fe(II), Cu, Mn, Ag, ammonium or substituted ammonium having one or more (C1-4)alkyl optionally substituted with one or more hydroxy;
   the "a" is an integer of from 1 to 3;
   the "b" is 1 or 2 equaling a valency of M; and
wherein the fermentation medium does not include other antimicrobial agents.

2. The fermentation medium according to claim 1, wherein R represents an acyl group with a straight or branched chain consisting of 12 to 14 carbon atoms.

3. The fermentation medium according to claim 2, wherein "a" in Formula 1 is 1.

4. A method for reducing microbial infections caused by gram-positive bacteria in a fermenter culture of at least one production strain of *E. coli* or *Salmonella enterica*, the method comprising:
   providing the fermentation medium of claim 1, comprising the at least one production strain of *E. coli* or *Salmonella enterica*; and
   culturing the at least one production strain of *E. coli* or *Salmonella enterica*, thereby producing a fermentation culture with reduced gram-positive microbial infections.

5. A method for obtaining a fermentation product from a fermenter culture of at least one production strain of *E. coli* or *Salmonella enterica*, the method comprising:
   providing the fermentation medium of claim 1, comprising the at least one production strain of *E. coli* or *Salmonella enterica*;
   culturing the at least one production strain of *E. coli* or *Salmonella enterica*, thereby producing the fermentation product;
   and
   isolating, purifying, and/or concentrating the fermentation product.

6. A fermentation medium comprising:
   an inoculant comprising a culture of at least one production strain of *E. coli*;
   a substrate for microbial growth, the substrate comprising one or more carbohydrates fermentable by the *E. coli* of the inoculant; and
   as an exogenously added ingredient, an antimicrobial agent comprising a lactylate in accordance with Formula 1 or salt thereof in an amount from 0.001 to 1.0 weight %, based on the total weight of the fermentation medium, $$(R-(O-CH(CH_3)-CO)_a O)_b M \quad \text{(Formula 1)};$$

wherein in the Formula 1:
   the "R" represents a C4-C18 acyl group, the acyl group having an alkyl or alkenyl chain which may be branched or unbranched;
   the "M" represents a proton (1-1±) or a counter-cation chosen from Li, Na, K, Ca, Mg, Zn, Fe(II), Cu, Mn, Ag, ammonium or substituted ammonium having one or more (C1-4)alkyl optionally substituted with one or more hydroxy;
   the "a" is an integer of from 1 to 3;
   the "b" is 1 or 2 equaling a valency of M; and
   wherein the fermentation medium does not include other antimicrobial agents.

7. The fermentation medium according to claim 6, wherein the fermentation medium comprises the lactylate in accordance with Formula 1 or the salt thereof in the amount from 0.001 to 0.05 weight %, based on the total weight of the fermentation medium.

8. The fermentation medium according to claim 6, wherein the fermentation medium comprises the lactylate in accordance with Formula 1 or the salt thereof in the amount from 0.025 to 1.0 weight %, based on the total weight of the fermentation medium.

* * * * *